US012564427B2

(12) United States Patent
Biedermann et al.

(10) Patent No.: US 12,564,427 B2
(45) Date of Patent: Mar. 3, 2026

(54) POLYAXIAL BONE ANCHORING DEVICE

(71) Applicant: BIEDERMANN TECHNOLOGIES GMBH & CO. KG, Donaueschingen (DE)

(72) Inventors: Lutz Biedermann, VS-Villingen (DE); Bernd Fischer, Bräunlingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 18/593,680

(22) Filed: Mar. 1, 2024

(65) Prior Publication Data

US 2024/0277380 A1     Aug. 22, 2024

Related U.S. Application Data

(63) Continuation of application No. 17/360,601, filed on Jun. 28, 2021, now Pat. No. 11,937,851, which is a
(Continued)

(30) Foreign Application Priority Data

Dec. 21, 2015     (EP) ..................................... 15201743

(51) Int. Cl.
    *A61B 17/70*     (2006.01)
    *A61B 17/00*     (2006.01)
    *A61B 17/56*     (2006.01)

(52) U.S. Cl.
    CPC ...... *A61B 17/7037* (2013.01); *A61B 17/7002* (2013.01); *A61B 17/7032* (2013.01);
    (Continued)

(58) Field of Classification Search
    CPC ........................................... A61B 17/70–7046
    See application file for complete search history.

(56) References Cited

U.S. PATENT DOCUMENTS

| 8,088,152 B2 | 1/2012 | Schumacher |
| 9,078,705 B2 | 7/2015 | Matthis et al. |

(Continued)

FOREIGN PATENT DOCUMENTS

| EP | 2 221 012 A1 | 8/2010 |
| EP | 2 674 123 A1 | 12/2013 |

(Continued)

OTHER PUBLICATIONS

Extended European Search Report for Application No. 15201743.0, dated Jun. 17, 2016, 7 pages.

*Primary Examiner* — Eduardo C Robert
*Assistant Examiner* — Steven J Cotroneo
(74) *Attorney, Agent, or Firm* — Womble Bond Dickinson (US) LLP

(57)     ABSTRACT

A polyaxial bone anchoring device includes a bone anchoring element having a head, a receiving part having a channel for receiving a rod and an accommodation space for pivotably holding the head, and a pressure member having a pressure exerting surface and a deformable portion with a free end. The deformable portion is adjustable from a first configuration where a first part of the deformable portion is supported at a first axial position relative to the receiving part while a second part of the deformable portion protrudes further radially into the channel than parts of the deformable portion positioned axially above the second part, to a second configuration where the second part of the deformable portion is deformed radially outwardly and the pressure exerting surface is shifted lower axially to exert pressure on the head while the first part of the deformable portion remains supported at the first axial position.

20 Claims, 11 Drawing Sheets

Related U.S. Application Data continuation of application No. 16/377,924, filed on Apr. 8, 2019, now Pat. No. 11,083,498, which is a continuation of application No. 15/385,368, filed on Dec. 20, 2016, now Pat. No. 10,285,737.

(60) Provisional application No. 62/270,304, filed on Dec. 21, 2015.

(52) U.S. Cl.
CPC *A61B 17/7035* (2013.01); *A61B 2017/00867* (2013.01); *A61B 2017/564* (2013.01)

(56) References Cited

U.S. PATENT DOCUMENTS

| | | | |
|---|---|---|---|
| 9,168,069 B2 | 10/2015 | Jackson et al. | |
| 9,572,600 B2 | 2/2017 | Biedermann et al. | |
| 9,763,702 B2 | 9/2017 | Schlaepfer et al. | |
| 9,980,753 B2* | 5/2018 | Jackson | A61B 17/7037 |
| 2006/0149235 A1 | 7/2006 | Jackson | |
| 2006/0155278 A1 | 7/2006 | Warnick | |
| 2008/0243193 A1 | 10/2008 | Ensign et al. | |

| | | | |
|---|---|---|---|
| 2009/0105770 A1 | 4/2009 | Berrevoets et al. | |
| 2009/0254125 A1 | 10/2009 | Predick | |
| 2010/0063550 A1 | 3/2010 | Felix et al. | |
| 2010/0160978 A1 | 6/2010 | Carbone | |
| 2010/0234902 A1* | 9/2010 | Biedermann | A61B 17/7037 606/305 |
| 2012/0253408 A1 | 10/2012 | Timm | |
| 2013/0197586 A1 | 8/2013 | Matthis et al. | |
| 2013/0338721 A1* | 12/2013 | Biedermann | A61B 17/7034 606/305 |
| 2013/0345761 A1 | 12/2013 | Biedermann et al. | |
| 2014/0025119 A1* | 1/2014 | Biedermann | A61B 17/7032 606/266 |
| 2014/0142634 A1* | 5/2014 | Schlaepfer | A61B 17/704 29/428 |
| 2016/0038204 A1* | 2/2016 | Biedermann | A61B 17/8605 606/305 |
| 2017/0172630 A1 | 6/2017 | Biedermann et al. | |
| 2017/0340360 A1* | 11/2017 | Schlaepfer | A61B 17/7037 |

FOREIGN PATENT DOCUMENTS

| | | |
|---|---|---|
| EP | 2 687 172 B1 | 1/2014 |
| WO | WO 2006/116437 A2 | 11/2006 |

* cited by examiner

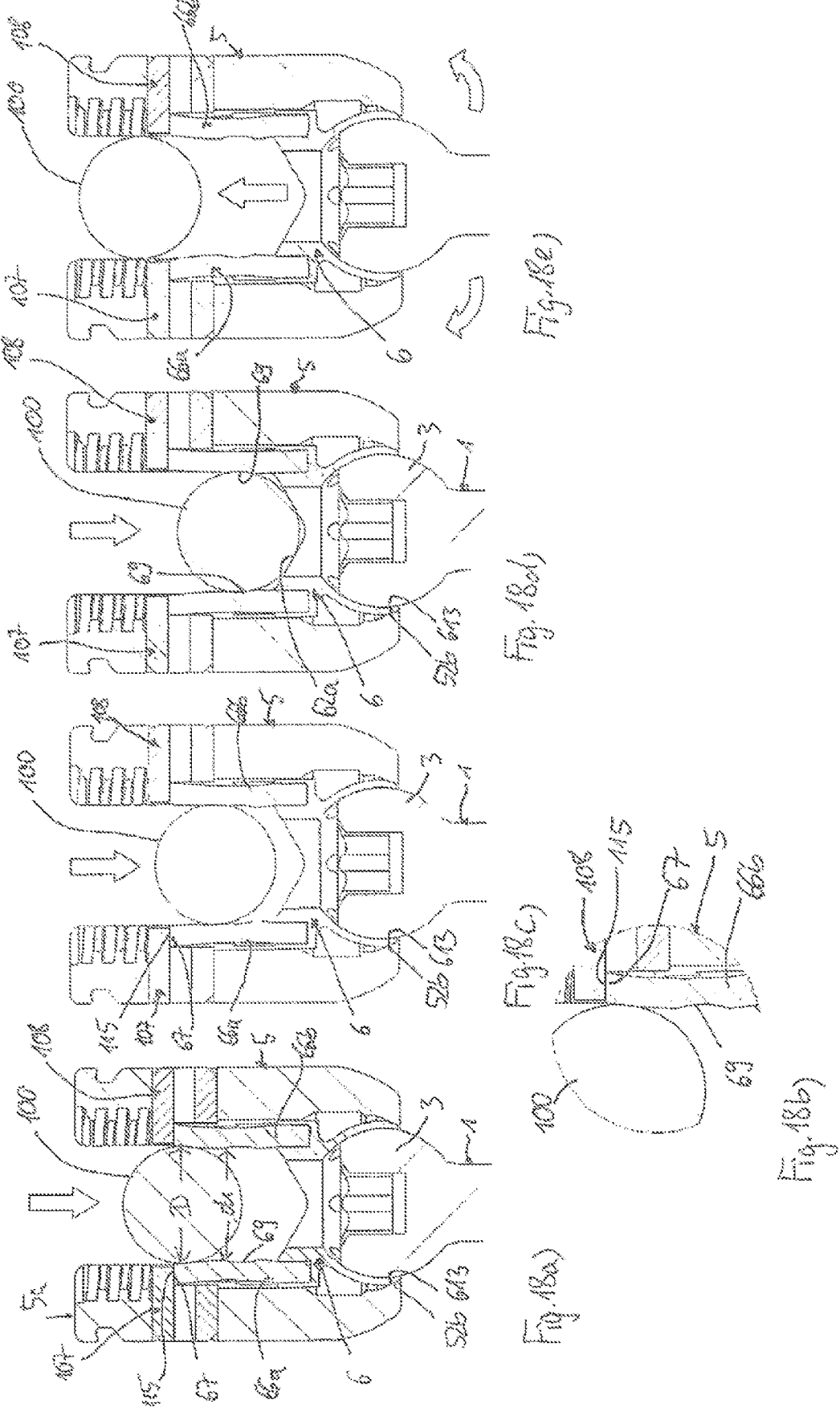

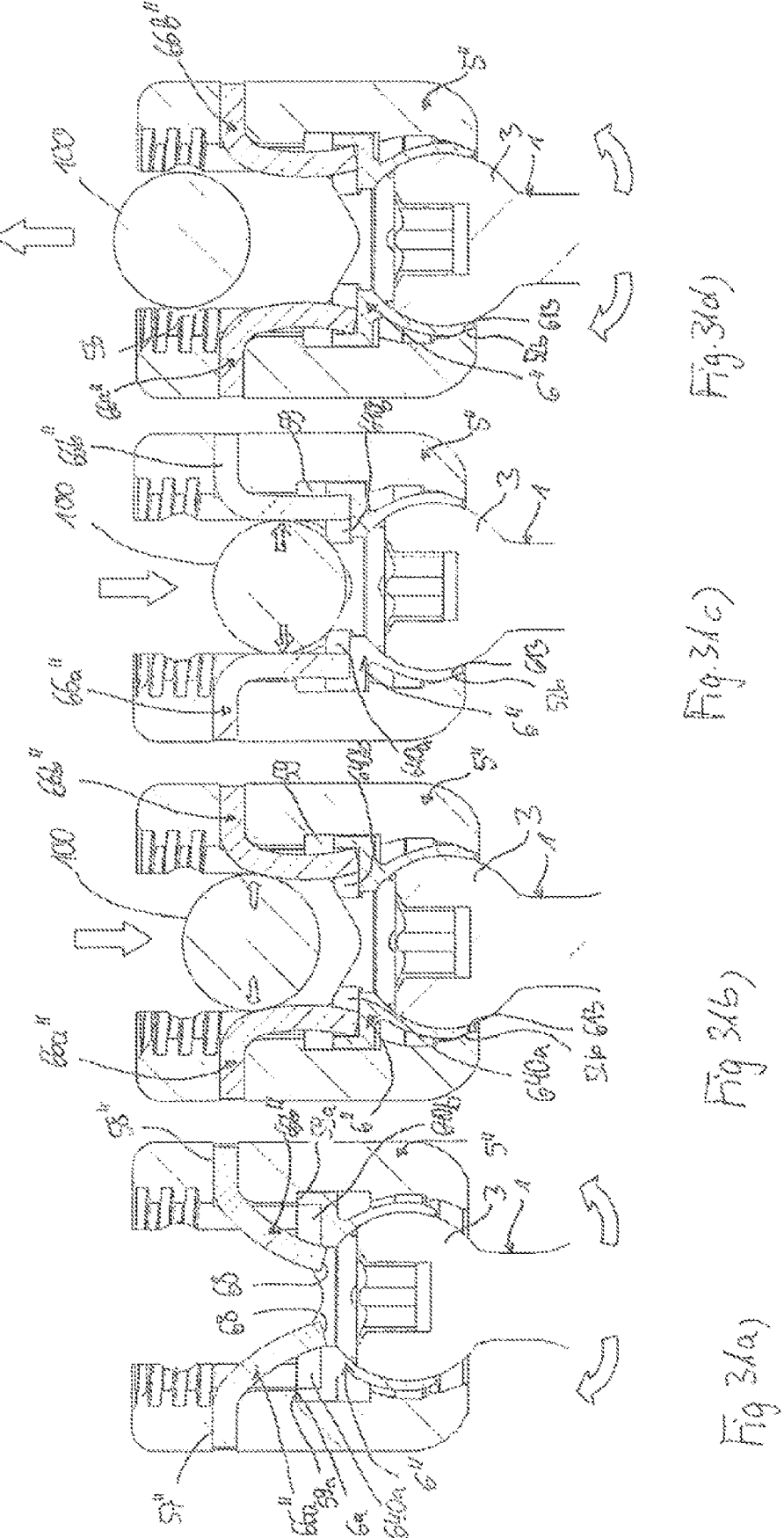

POLYAXIAL BONE ANCHORING DEVICE

CROSS-REFERENCE TO RELATED APPLICATION(S)

This application is a continuation of U.S. patent application Ser. No. 17/360,601, filed Jun. 28, 2023, which is a continuation of U.S. patent application Ser. No. 16/377,924, filed Apr. 8, 2019, now U.S. Pat. No. 11,083,498, which is a continuation of U.S. patent application Ser. No. 15/385, 368, filed Dec. 20, 2016, now U.S. Pat. No. 10,285,737, which claims the benefit of U.S. Provisional Patent Application Ser. No. 62/270,304, filed Dec. 21, 2015, and claims priority from European Patent Application EP 15 201 743.0, filed Dec. 21, 2015, the contents of which are hereby incorporated by reference in their entirety.

BACKGROUND

Field

The invention relates to a polyaxial bone anchoring device for coupling a bone anchoring element to a rod. The polyaxial bone anchoring device includes a receiving part, a bone anchoring element with a head and a shank, and a rod. The receiving part has a channel for receiving the rod and an accommodation space for pivotably holding the head of the bone anchoring element. The head can be locked at an angle relative to the receiving part by applying pressure onto the head via a pressure member, where the pressure member includes a deformable portion. The deformable portion can be deformed by the rod so that the head is firmly clamped or locked in the receiving part. The bone anchoring element of the polyaxial bone anchoring device can be held or maintained at a particular angular position by only using the rod, for example, without using an additional locking member.

Description of Related Art

US 2013/0345761 A1 describes a polyaxial bone anchoring device including a bone anchoring element with a shank and a head wherein the head is pivotably coupled to a receiving part which has a channel for receiving a rod. A pressure member is arranged in a receiving part and configured to exert pressure onto the head to lock the head in the receiving part. The pressure member has a deformable portion. Load applied to the pressure member by a locking member clamps the head and thereafter the locking member contacts the pressure member such that the deformable portion is deformed and the locking member comes into contact with the rod and clamps the rod.

SUMMARY

Embodiments of the invention provide an improved polyaxial bone anchoring device for coupling a rod to a bone anchoring element, where the bone anchoring device can have more flexibility and can be easier to use during surgery.

The polyaxial bone anchoring device includes a pressure member that exerts pressure onto a head of the bone anchoring element, where the pressure member has a deformable portion with a free end that is supported in a receiving part of the bone anchoring device. The deformable portion can be deformed from a first configuration into a second configuration. Due to the deformation, the pressure exerted by the pressure member onto the head increases. Hence, the deformable portion functions similar to a toggle lever that transforms or adjusts from an angled configuration into a less angled or substantially straight configuration. The deformable portion of the pressure member can be deformed from the first configuration into the second configuration by inserting the rod into the channel. By means of this, the head can be fixed at an angular position with respect to the receiving part only by inserting the rod, for example, without the use of an additional locking member, such as a set screw. This allows the surgeon to perform various adjustments of the position of the receiving part relative to the rod without the locking member inserted. Thereby, the handling of the device during surgery can be considerably improved. The deformable portion may be formed by one or more deformable elements.

By selecting the design of the deformable portion of the pressure member, the head can either be locked, or can be held by friction in an adjustable angular position that can be changed by applying a force greater than the friction force to the receiving part, when the rod is inserted.

In one embodiment, the rod can be retained in the channel by the pressure member. By means of this, the rod is prevented from slipping out of the channel. In a further embodiment, the rod can be held in the channel by friction in a manner such that the position of the rod relative to the receiving part can be changed by applying a force that overcomes the friction. This facilitates adjustments to the position of the rod in certain procedures.

In a further embodiment, the clamping or locking of the head can be released by moving the rod out of the channel.

In a still further embodiment, the clamping or locking of the head is maintained even if the rod is moved out of the channel. In some of these embodiments, the clamping or locking of the head can be released, for example, by applying an instrument that brings the deformable portion from the second configuration back to the first configuration. This may be advantageous in a case where the rod needs to be freely movable for adjustment steps while the angular position of the anchoring element should be maintained.

The polyaxial bone anchoring device is of the bottom loading type, wherein the head of the bone anchoring element is inserted in to the receiving part from a bottom side, or from the side opposite to the side on which the rod is inserted. With this design, a modular system can be provided that allows combining of a variety of different bone anchoring elements with the receiving part to form the polyaxial bone anchoring device.

In a further embodiment, the deformable portion cooperates with the receiving part to hold the pressure member in an insertion position in which the head of the bone anchoring element can be inserted through the bottom end of the receiving part. The deformable portion also may cooperate with the receiving part to hold the pressure member in a pre-locking position, in which the head has been inserted into the receiving part and is prevented from removal therefrom.

In a further embodiment, the deformable portion of the pressure member is elastically deformable and includes a highly elastic material, in particular, a material with super-elastic properties, such as a nickel-titanium (NiTi)-alloy, for example, Nitinol, or, for example, beta-titanium. Due to the elasticity of the deformable portion, size tolerances of the pressure member and the parts interacting therewith can be balanced.

A locking member or locking device may be provided to finally lock the polyaxial bone anchoring device with respect to the head and the rod.

BRIEF DESCRIPTION OF THE DRAWINGS

Further features and advantages of the invention will become apparent from the description of the embodiments, by means of the accompanying drawings. In the drawings:

FIG. 18a shows a cross-sectional view of a step of inserting the rod into the polyaxial bone anchoring device according to the first embodiment.

FIG. 18b shows an enlarged view of a detail of FIG. 18a.

FIGS. 18c to 18e show cross-sectional views of further steps of use of the polyaxial bone anchoring device according to the first embodiment with a rod.

FIGS. 31a to 31d show cross-sectional views of steps of using the polyaxial bone anchoring device of the third embodiment together with a rod.

DETAILED DESCRIPTION

Figures 1, 2:
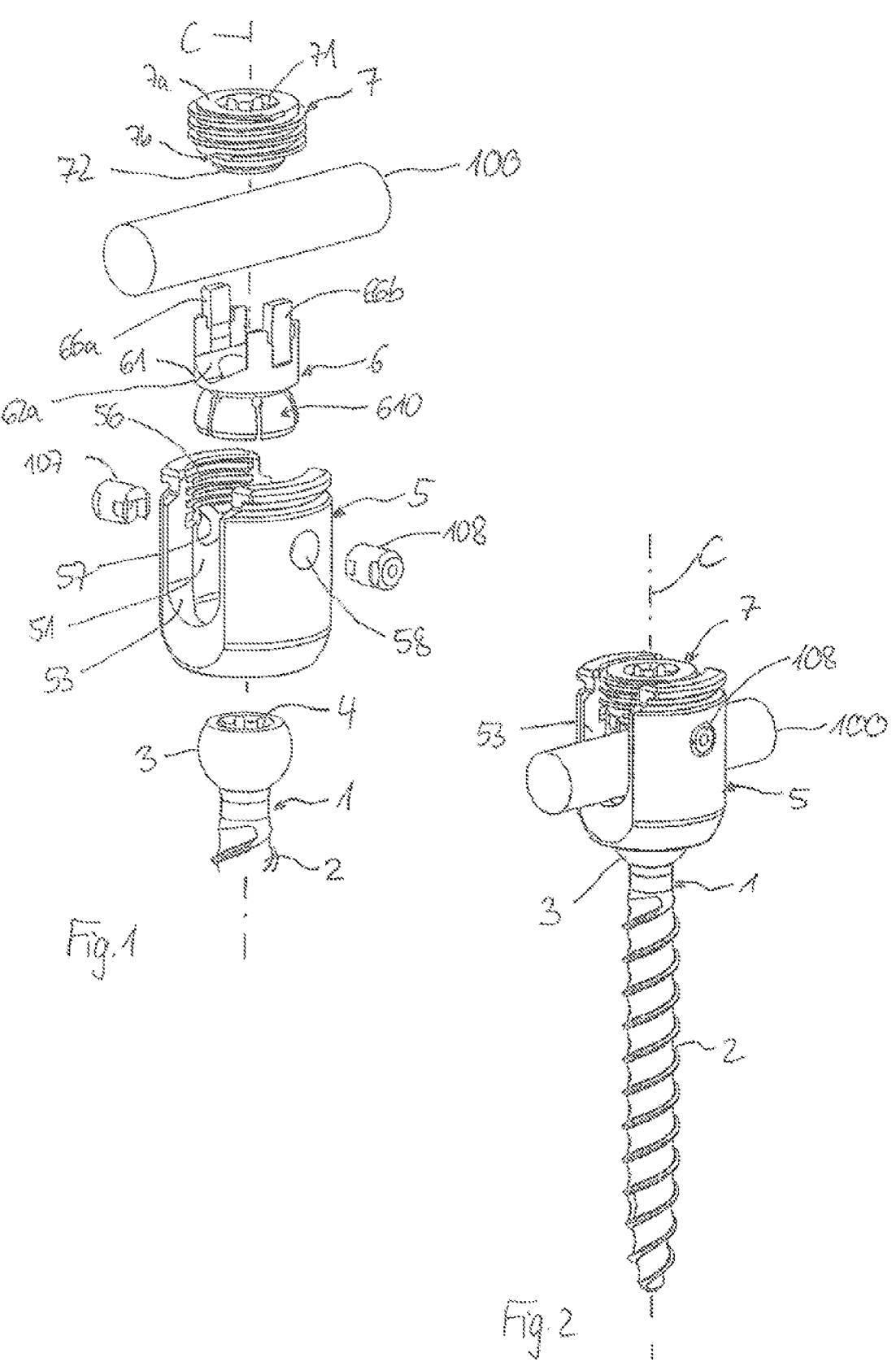
FIG. 1 shows a perspective exploded view of a polyaxial bone anchoring device according to a first embodiment.
FIG. 2 shows a perspective view of the polyaxial bone anchoring device according to FIG. 1 in an assembled state with the rod inserted.

A polyaxial bone anchoring device according to a first embodiment is shown in FIGS. 1 and 2. The polyaxial bone anchoring device includes an anchoring element 1 having a shank 2 with a threaded portion and a head 3. The head 3 has a spherically-shaped outer surface portion and, on its side opposite to the shank 2, a recess 4 for engagement with a tool. A receiving part 5 is provided for coupling the bone anchoring element 1 to a rod 100. In addition, a pressure member 6 configured to be arranged in the receiving part 5 is provided to exert pressure onto the head 3 of the bone anchoring element 1. For locking the head 3 and the rod 100 relative to the receiving part 5, the polyaxial bone anchoring device may further include a locking member 7 that is insertable into the receiving part 5. The polyaxial bone anchoring device in this embodiment is of the bottom loading type, i.e., the head 3 of the bone anchoring element 1 can be inserted into the receiving part 5 from a bottom end of the receiving part 5.

Referring further to FIGS. 3 to 7, the receiving part 5 has a first end or top end 5a and a second end or bottom end 5b, and has a substantially cylindrical construction with a central longitudinal axis C that goes through the top end 5a and the bottom end 5b. Coaxial with the longitudinal axis C, a first bore 51 is provided that extends from the top end 5a to a distance from the bottom end 5b. A hollow space that is substantially rotationally symmetrical is formed between the bottom end 5b and the first bore 51, which serves as an accommodation space 52 for the head 3. The accommodation space 52 has a bottom opening 52a with an inner diameter at the bottom end 5b that is greater than an outer diameter of the head 3. This permits the insertion of the head 3 through the opening 52a from the bottom end 5b. The accommodation space 52 further has a greater diameter approximately in the middle between the junction to the coaxial bore 51 and the opening 52a. The size of the accommodation space 52 is such that the pressure member 6 can be expanded therein when the head 3 is inserted. Adjacent to the opening 52a, there is a narrowing portion 52b that is configured to engage a narrowing portion of the pressure member 6. The narrowing portion 52*b* may have a tapered shape or a spherical segment-shape, or any other shape that permits the compression of a lower end of the pressure member 6. An edge 52*c* may be formed at a distance from the bottom end 5*b* that protrudes into the accommodation space 52 and that may contribute to the compression of the pressure member 6.

The receiving part 5 further has a U-shaped recess 53 extending from the top end 5*a* in the direction of the bottom end 5*b*. By means of the U-shaped recess 53, two free legs 54, 55 are formed that define a channel for receiving the rod 100. Adjacent to the top end 5*a*, an internal thread 56 is provided at the inner surface of the legs 54, 55. In the embodiment shown, the internal thread 56 is a flat thread having substantially horizontal upper and lower thread flanks. Any other thread form can be used for the internal thread 56.

Figures 4, 5, 6, 7:
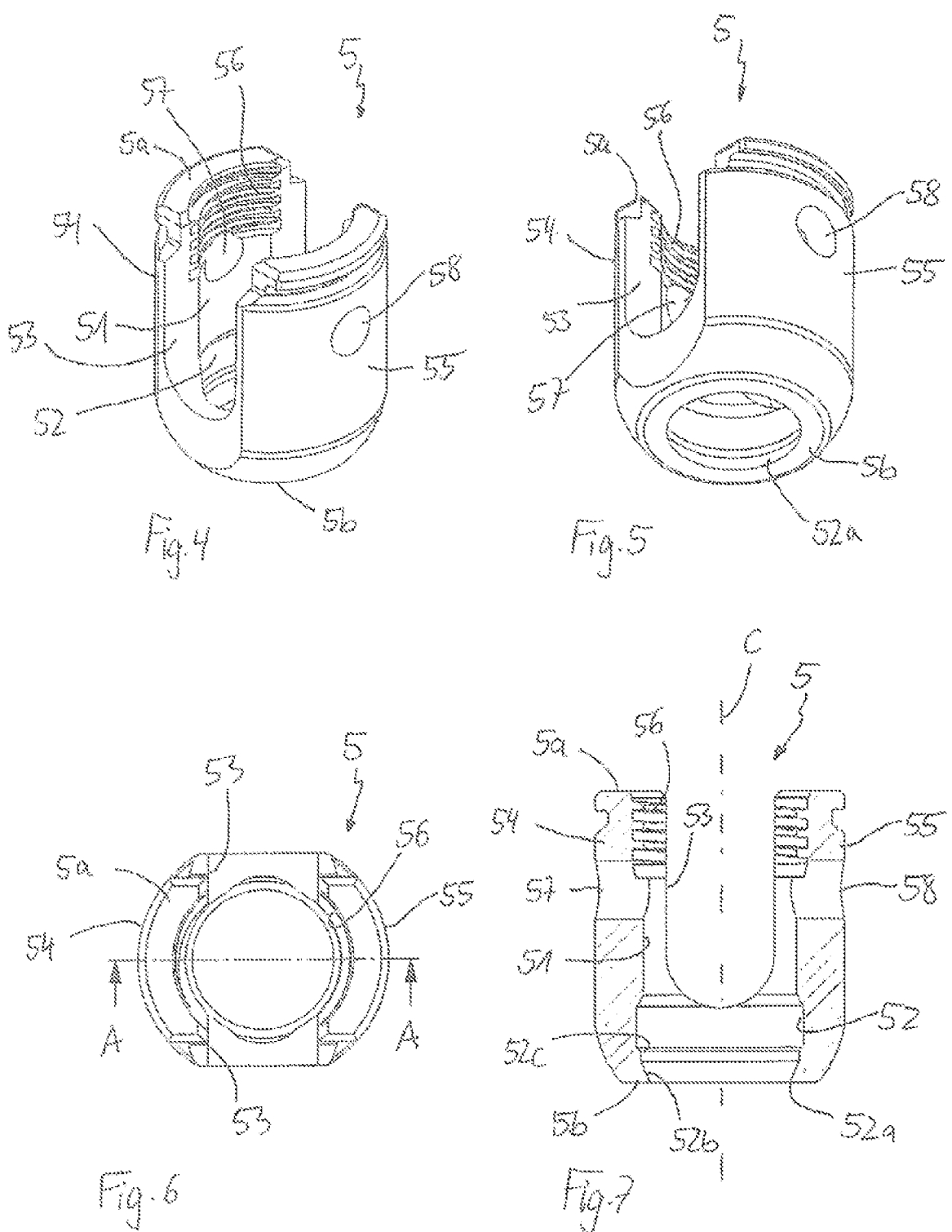
FIG. 4 shows a perspective view from a top of a receiving part of the polyaxial bone anchoring device according to FIGS. 1 to 3.
FIG. 5 shows a perspective view from a bottom of the receiving part of FIG. 4.
FIG. 6 shows a top view of the receiving part of FIGS. 4 and 5.
FIG. 7 shows a cross-sectional view of the receiving part of FIGS. 4 to 6, the cross-section taken along line A-A in FIG. 6.
Figures 8, 9, 10, 11, 12:
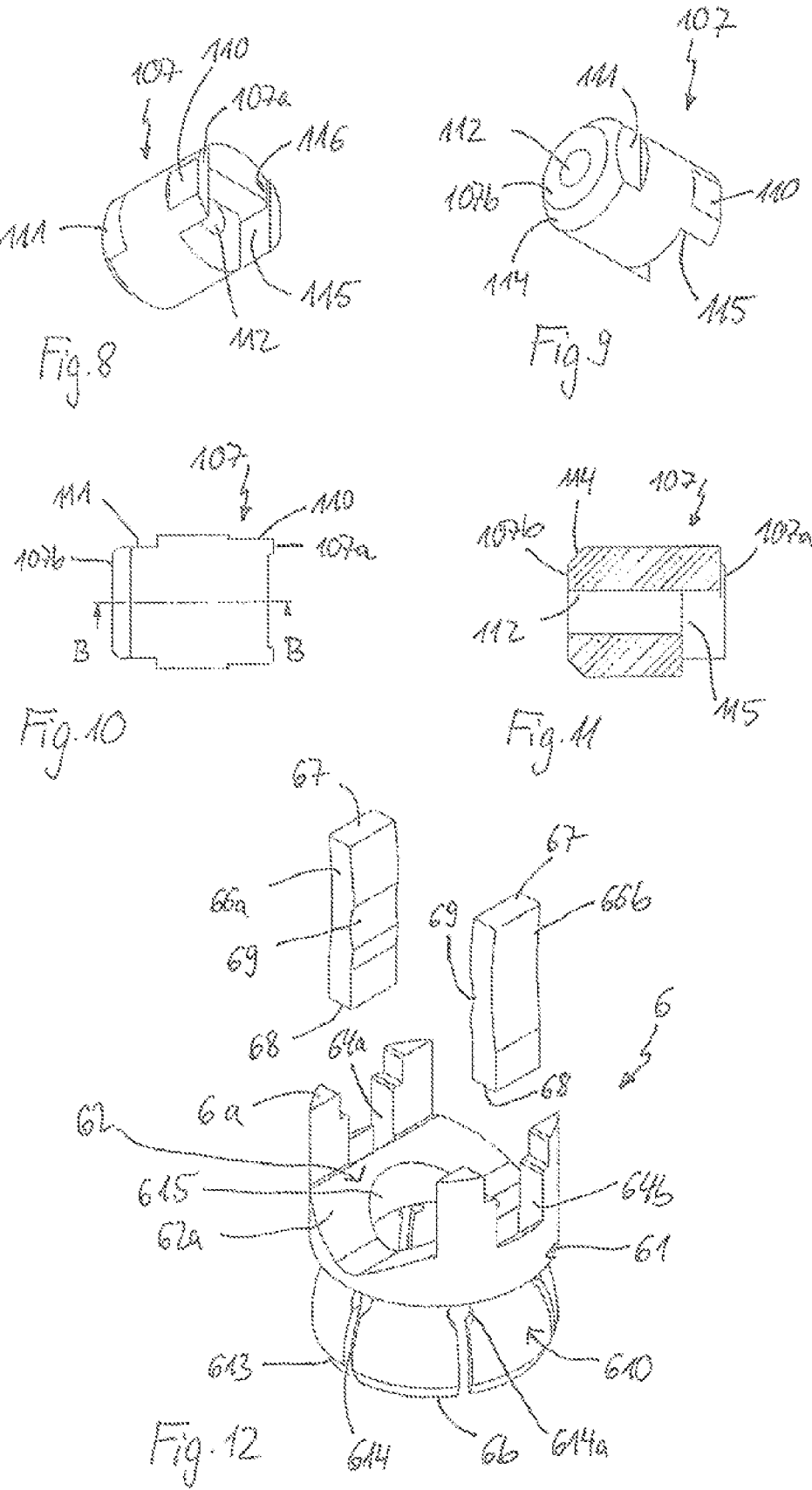
FIG. 8 shows a perspective view from a front of a pin member used in the poly-axial bone anchoring device according to FIGS. 1 to 3.
FIG. 9 shows a perspective view from the rear side of the pin member of FIG. 8.
FIG. 10 shows a top view of the pin member of FIGS. 8 and 9.
FIG. 11 shows a cross-sectional view of the pin member of FIGS. 8 to 10, the cross-section taken along line B-B in FIG. 10.
FIG. 12 shows a perspective exploded view of a pressure member of the polyaxial bone anchoring device of FIGS. 1 to 3.
Figures 13, 14, 15, 16:
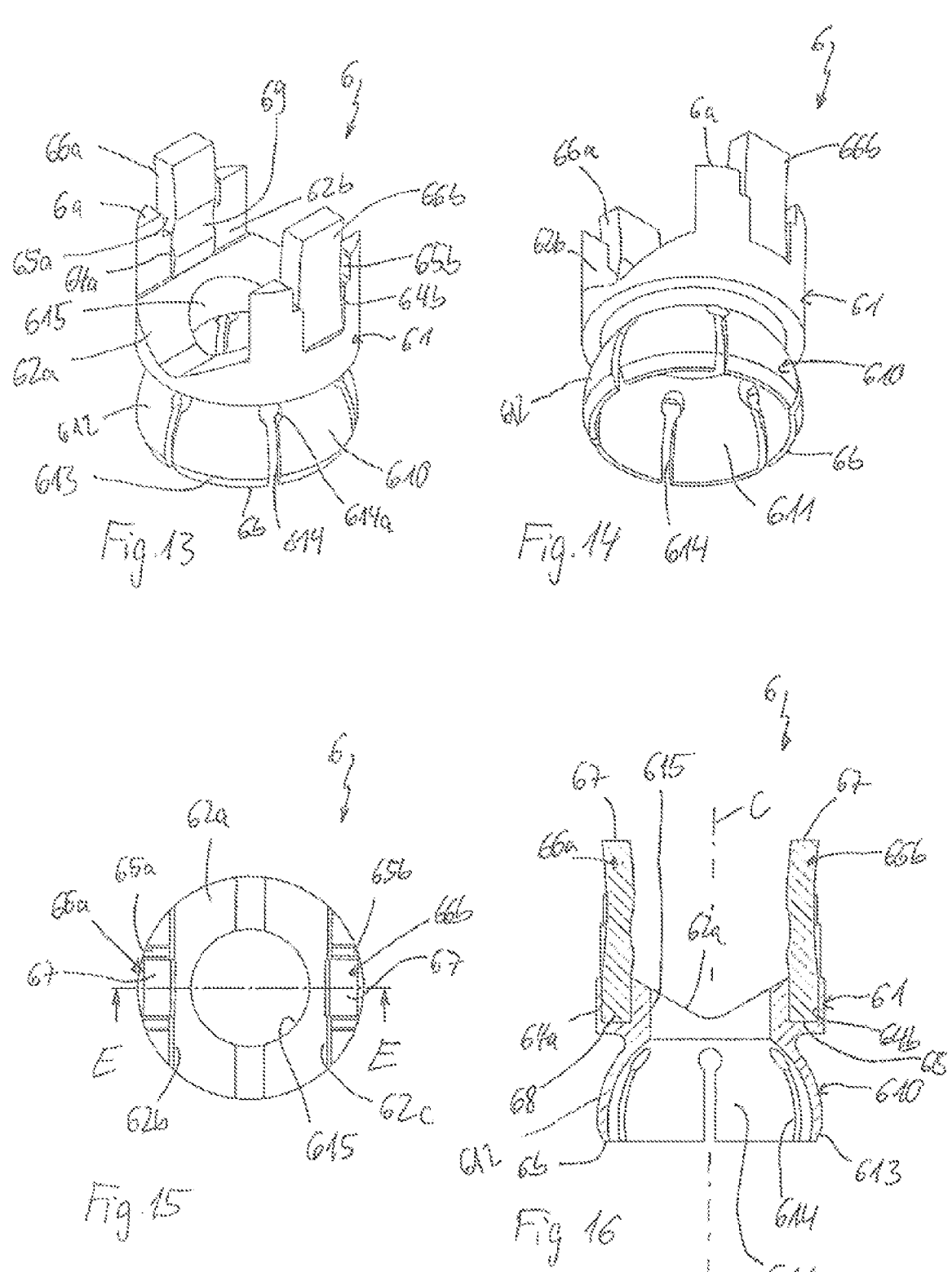
FIG. 13 shows a perspective view from a top of the pressure member of FIG. 12 in an assembled state.
FIG. 14 shows a perspective view from a bottom of the assembled pressure member of FIG. 13.
FIG. 15 shows a top view of the assembled pressure member of FIGS. 13 and 14.
FIG. 16 shows a cross-sectional view of the assembled pressure member of FIGS. 13 to 15, the cross-section taken along line E-E in FIG. 15.

As shown best in FIGS. 4 and 7, in each of the legs 54, 55 a transverse hole 57, 58, respectively, is formed that extends completely through the wall of the receiving part 5 in a direction perpendicular to the longitudinal axis C. The transverse holes 57, 58 serve for accommodating pin members 107, 108 therein.

Figure 3:
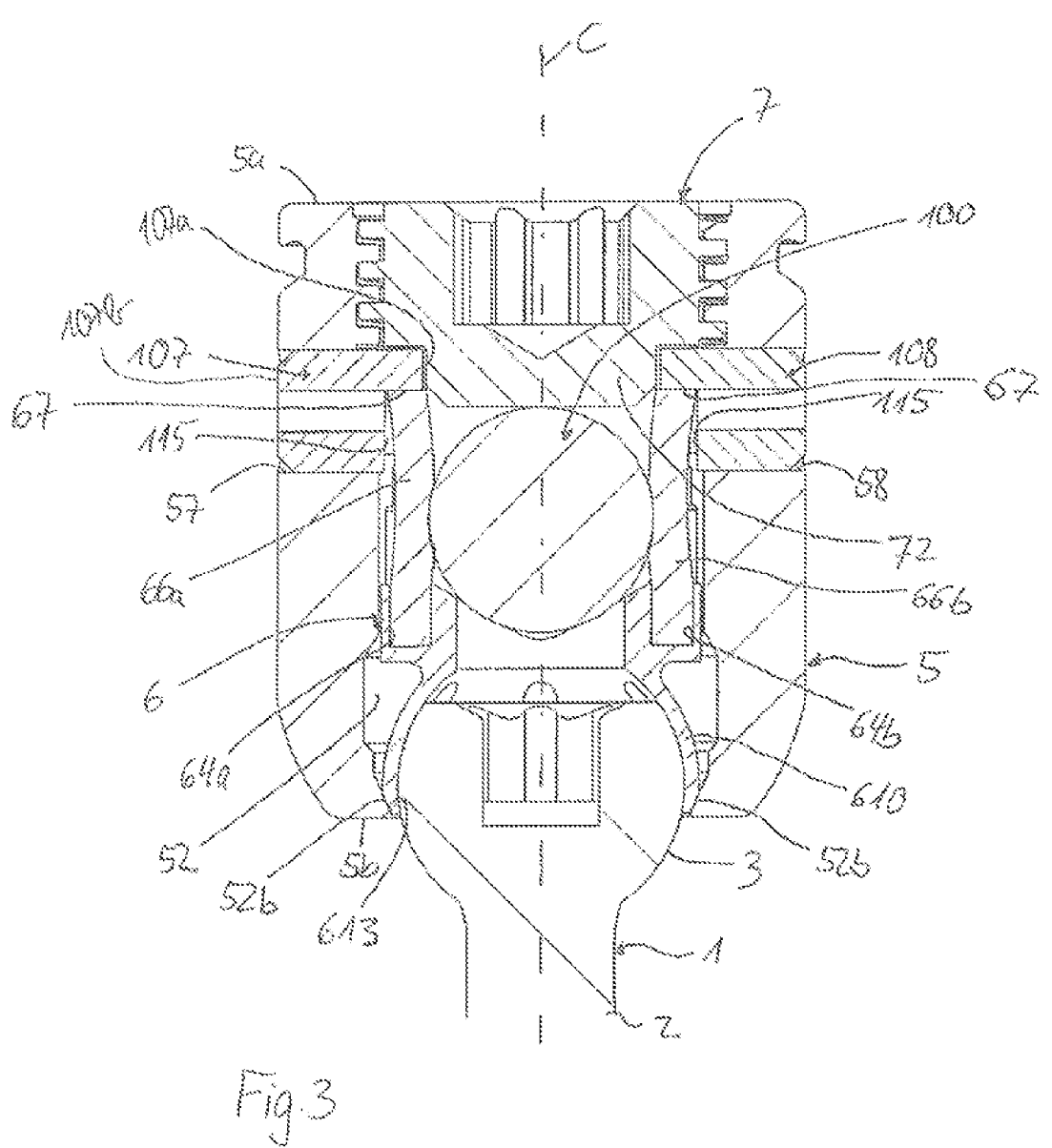
FIG. 3 shows a cross-sectional view of the polyaxial bone anchoring device according to FIGS. 1 and 2 in an assembled and locked state, the cross-section taken in a plane perpendicular to an axis of the inserted rod and extending through the central axis of the receiving part.

The pin members 107, 108 are substantially cylindrical parts, with a largest outer diameter that is sized such that the pin members 107, 108 can be inserted, for example, in a press-fit manner into the transverse hole 57, 58 of receiving part 5, as depicted in greater detail in FIG. 3. FIGS. 8 to 11 provide more detailed views of pin member 107 as an example, where pin member 108 can be configured similarly. Referring now to FIGS. 8 to 11, pin member 107 has a front surface 107*a* configured to face towards the coaxial first bore 51 of the receiving part 5 and a rear surface 107*b* configured to face towards the outside of the receiving part 5 when the pin member 107 is in a mounted state. Adjacent to the front end 107*a*, two substantially flat front engagement recesses 110 are formed on opposite sides of the pin member 107, that serve for holding the pressure member 6 at an insertion position relative to the receiving part 5. Similarly, two substantially flat rear engagement recesses 111 are formed adjacent to the rear side 107*b*, on opposite sides from one another, and on the same sides as the front engagement recesses 110. The rear engagement recesses 111 are configured to be engaged with a tool. The engagement recesses 111 serve for facilitating assembly or disassembly of the pin members 107, 108 with the receiving part 5. Furthermore, each pin member 107, 108 has a coaxial central bore 112 that extends completely through the pin member and that permits guiding of an instrument or tool therethrough. The pin members 107, 108 may each have a chamfer 114 at the rear end (e.g., 107*b*) for facilitating insertion into and/or removal from the receiving part 5. An axial length of the pin members 107, 108 is such that when the pin members 107, 108 are inserted into the transverse holes 57, 58, respectively, and their rear surfaces (e.g., 107*b*) are flush with the outer surface of the receiving part 5, the front surfaces (e.g., 107*a*) extend into the coaxial first bore 51, as depicted in FIG. 3.

Moreover, each pin member 107, 108 has a first front recess 115 that has a substantially rectangular contour or cross-section, and that serves for accommodating and supporting a free end portion of the pressure member 6 therein. A second front recess 116 that is less deep than the first front recess 115 is formed at a position between the front engagement recesses 110. The second front recess 116 may serve for holding a portion of the pressure member 6 when the pressure member 6 is at the insertion position.

Next, the pressure member 6 will be described with reference to FIGS. 12 to 16. The pressure member 6 has a substantially cylindrical first portion 61 with a top surface 6*a*. An outer diameter of the first portion 61 is such that the first portion 61 fits into the coaxial first bore 51 of the receiving part 5. A recess 62 extends from the top surface 6*a* of the first portion 61 into the first portion 61, thereby also forming a channel for the rod 100. The recess 62 has in a cross-sectional view, a substantially V-shaped bottom 62*a*, as can be seen in particular in FIG. 16, and two opposite flat side walls 62*b*, 62*c* (see, e.g., FIG. 15). The bottom 62*a* provides a rod supporting surface in the form of a V-groove that is configured to support rods of different diameters, so that each rod can be safely supported along two contact lines along and in the direction of the V-groove. At approximately the centers of the sidewalls 62*b*, 62*c*, recesses 64*a*, 64*b* are respectively formed and extend in an axial direction. The recesses 64*a*, 64*b* serve for accommodating deformable elements 66*a*, 66*b* therein. The recesses 64*a*, 64*b* each has a widened portion 65*a*, 65*b*, respectively, towards the upper surface 6*a*. The size of the widened portions 65*a*, 65*b* are such that the pressure member 6 can frictionally engage the recesses 110 of the pin members 107, 108. As can be seen more in detail in FIG. 16, the recesses 64*a*, 64*b* extend into the first portion 61, to a depth of or close to the bottom 62*a* of the rod recess 62. This allows for insertion and holding of the deformable elements 66*a*, 66*b* therein. The deformable elements 66*a*, 66*b* each has a first end or free end 67 and an opposite second end 68 that is mounted at the recesses 64*a*, 64*b*, respectively. In a neutral configuration the deformable elements 66*a*, 66*b* protrude upwards (e.g., as shown in FIGS. 13 to 16) and exhibit a slight curvature in the longitudinal direction, where at least a central region of each deformable element 66*a*, 66*b* curves or bows towards a center of the rod channel. At inner surfaces of the deformable element 66*a*, 66*b*, a shallow transverse groove 69 is provided. When the deformable elements 66*a*, 66*b* are mounted to the first portion 61, the deformable elements 66*a*, 66*b* extend above the top surface 6*a*.

The deformable elements 66*a*, 66*b* may be elastically deformable in such a manner that they can be deflected outward by an applied load and return to their neutral shape and position once the load is relieved or released. Preferably, the deformable elements 66*a*, 66*b* are made from a material exhibiting high elasticity, such as a nickel-titanium alloy, that has super-elastic properties, for example Nitinol, or beta-titanium.

The pressure member 6 further includes on a side opposite to the top surface 6*a* a second portion 610 that is recessed with respect to the first portion 61, a lower edge of which forms a second end or bottom end 6*b* of the pressure member 6. The second portion 610 has a hollow interior 611 which is substantially spherically-shaped to clamp the spherical head 3 therein, and that is open at the second end 6*b*. An inner surface of the second portion 610 is configured to contact the head 3 and forms a pressure exerting surface. An outer wall of the second portion 610 includes a substantially spherical first portion 612 and a narrowing portion 613 that narrows towards the second end 6*b*. The narrowing portion 613 is configured to cooperate with the narrowing portion 52*b* of the receiving part 5. The narrowing portion 613 may be tapered or spherical, or shaped in another manner, and may not necessarily correspond to the shape of the narrowing portion 52*b* of the receiving part 5, as long as the narrowing portion 613 can be compressed by the narrowing portion 52*b* of the receiving part 5. The second portion 610 of the pressure member 6 further has a plurality of slits 614 extending from the free end 6*b* through the second portion 610. The number and dimensions of the slits 614 are such that the wall of the second portion 610 is flexible enough to snap onto the head 3 when the head 3 is inserted therein. The slits 614 may have enlarged portions 614*a* at their closed ends. A coaxial bore 615 extends through the first portion 61 and into the hollow interior 611 of the second portion 610 for providing access to the head 3 of the anchoring element 1 with an instrument.

Turning now to FIGS. 1 and 2 again, the locking member 7 may be a set screw with a top surface 7*a* and an opposite bottom surface 7*b*, and an external thread that cooperates with the internal thread 56 of the receiving part 5. In the top surface 7*a*, a recess 71 is provided for engagement with a driver. From the bottom surface 7*b*, a central projection 72 protrudes that is substantially cylindrical and has an outer diameter that is smaller than a distance between the front surfaces of the pin members 107, 108 when the pin members 107, 108 are inserted into the transverse holes 57, 58 of the receiving part 5, and the rear surfaces of the pin members 107, 108 are flush with the outer surface of the receiving part 5. As can be seen in greater detail in FIG. 3, an axial length of the projection 72 is such that when the locking member 7 is screwed into the receiving part 5, the end surface of the projection 72 can engage an inserted rod 100.

The receiving part 5, the pressure member 6, with or without the deformable elements 66*a*, 66*b*, the bone anchoring element 1, and the locking member 7 can each be made of any body-compatible material, such as a body-compatible metal or a metal alloy, such as stainless steel, a titanium, a magnesium, or a body-compatible plastic, such as polyether ether ketone (PEEK) or poly-L-lactide acid (PLLA). The parts can all be made of the same material or materials, or of different materials. The entire pressure member 6 may be made of the above-mentioned material exhibiting high elasticity, or only the deformable elements 66*a*, 66*b* may be made of such material.

Figures 17A, 17B, 17C:
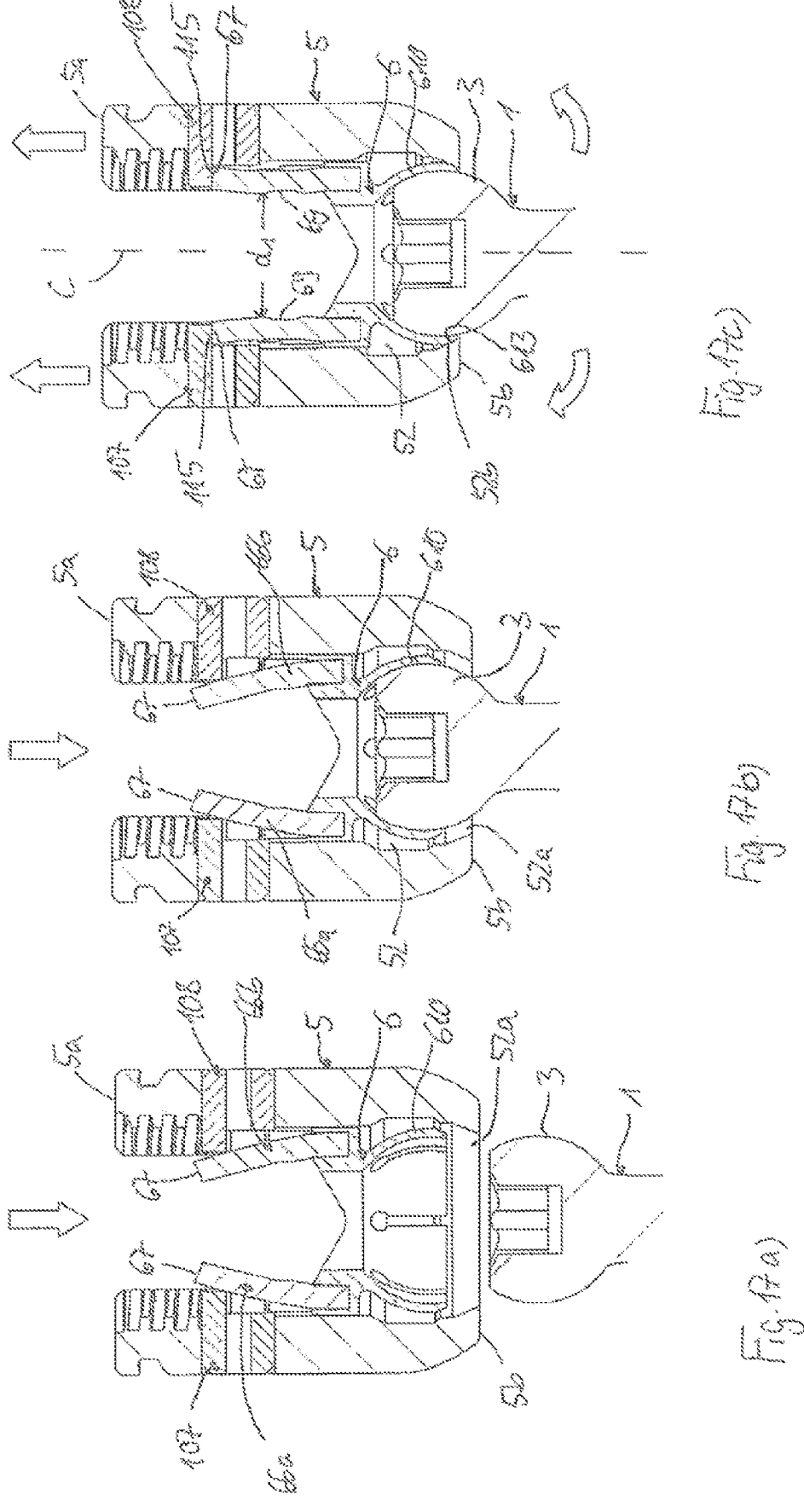
FIGS. 17a to 17c show cross-sectional views of steps of assembling the bone anchoring element and the receiving part of the polyaxial bone anchoring device according to the first embodiment.

Referring now to FIGS. 17*a* to 17*c*, the assembly of an embodiment of the polyaxial bone anchoring device is as follows. As illustrated in FIG. 17*a*, the pressure member 6, with the deformable elements 66*a*, 66*b* pre-mounted into the recesses 64*a*, 64*b*, is pre-assembled with the receiving part 5 in a manner such that the inserted pin members 107, 108 press the deformable elements 66*a*, 66*b* slightly towards each other. This is an insertion position of the pressure member 6, where the second portion 610 is arranged in the accommodation space 52 and has room to expand therein. The pressure member 6 is held in the insertion position by the pin members 107, 108. To achieve this, the sidewalls 62*b*, 62*c* of the pressure member 6 engage the engagement recesses 110 of the pin members 107, 108, such that the pressure member 6 slightly clamps or engages the pin members 107, 108 by friction. Next, as depicted in FIG. 17*b*, the head 3 of the bone anchoring element 1 is inserted through the bottom opening 52*a* and introduced into the hollow interior 611 of the second portion 610 of the pressure member 6. The pressure member 6 cannot move upward in the insertion position, since the inserted pin members 107, 108 act as a stop for the deformable elements 66*a*, 66*b*, and in some embodiments, through engagement with the widened portions 65*a*, 65*b*. By means of this, the second portion 610 of the pressure member 6 can snap over the head 3.

Thereafter, as can be seen in FIG. 17*c*, the receiving part 5 is pulled upward relative to the bone anchoring element 1, so that the deformable elements 66*a*, 66*b* can snap into the recesses 115 of the pin members 107, 108, respectively. The free ends 67 of the deformable elements are supported by an upper wall of the recesses 115. Simultaneously, narrowing portion 613 of the pressure member 6 is advanced to the narrowing portion 52*b* of the accommodation space 52. In this pre-locking position the head 3 is prevented from removal through the bottom opening 52*a*. Depending, for example, on the size of the head 3 in relation to the hollow interior 611 of the pressure member 6, the head 3 may be held by means of friction within the second portion 610 of the pressure member 6. This allows adjustments of an angular position of the receiving part 5 relative to the bone anchoring element 1 to a desired position, and for the adjusted position to be temporarily held. As further depicted in FIG. 17*c*, the deformable elements 66*a*, 66*b* are bent slightly inwards, and the shallow rod retention grooves 69 face towards the central axis C. In the pre-locking position, at least a portion of the deformable elements 66*a*, 66*b* protrudes into the rod channel, to an extent such that a smallest distance $d_1$ between the inner walls of the deformable elements 66*a*, 66*b* in a direction perpendicular to the central axis is smaller than a diameter D of the rod 100. Hence, when the rod 100 passes the smallest distance $d_1$, the rod 100 will deform the deformable elements 66*a*, 66*b* (e.g., radially outwards) in order to move forward or further downwards into the channel. As can be further seen in FIG. 17*c*, between an outer surface of the deformable elements 66*a*, 66*b* and an inner surface of the receiving part 5, there are gaps that permit the deformable elements 66*a*, 66*b* to deform radially outwardly.

Turning now to FIGS. 18*a* and 18*b*, when the rod 100 having the diameter D is inserted from the top end 5*a* of the receiving part 5 and between the deformable elements 66*a*, 66*b*, the rod 100 passes the position of the deformable elements 66*a*, 66*b* defining the smallest distance $d_1$. The rod 100 exerts a force onto the deformable elements 66*a*, 66*b* that bends the deformable elements 66*a*, 66*b*, as can be seen in FIG. 18*c*. Like with a toggle-lever, this straightens the deformable elements 66*a*, 66*b*, which in turn results in a downward movement of the bottom of the pressure member 6, which increases the pressure onto the head 3. When the rod 100 has been completely inserted relative to the pressure member 6 and rests on the rod supporting surface 62*a* of the pressure member 6, the rod 100 extends into the rod retention grooves 69 and is held therein. Depending on the size and shape of the deformable elements 66*a*, 66*b*, the rod 100 can be strongly clamped therein, or slightly held by friction so that the rod 100 can still be moved by applying a force greater than the friction force. In the second configuration shown in FIG. 18*d*, the pressure member 6 has been moved deeper into the narrowing portion 52*b* of the receiving part 5 such that the head 3 is locked or almost locked.

In clinical use, the bone anchoring device can be, for example, pre-assembled in such a way that a suitable bone anchoring element 1 is selected and inserted into the receiving part 5 with inserted pressure member 6. The bone anchoring device can then be implanted into a bone. In an alternative manner, the bone anchoring element 1 can first be implanted into the bone, and thereafter the receiving part 5 with the pressure member 6 can be mounted onto the head 3 of the bone anchoring element 1. Usually at least two bone anchoring elements 1 are inserted into bone parts or adjacent vertebrae and the receiving parts 5 are aligned to receive the rod 100. Then, the rod 100 is inserted into the receiving parts 5, thereby locking or strongly clamping the heads 3 with respect to the receiving parts 5. In the second configuration of the pressure member 6 the position of the rod 100 can be easily adjusted while the heads 3 are maintained at specific or temporarily held angular positions relative to their corresponding receiving parts. This facilitates easier handling, as locking members 7 are not needed for this procedure.

If desired, as depicted in FIG. 18e, when the rod 100 is removed from the receiving part 5, in some embodiments, the deformable elements 66a, 66b resume the first configuration in which the deformable elements 66a, 66b are slightly bent inwards. As a consequence thereof, the pressure onto the head 3 is released, and the head 3 becomes freely pivotable in the receiving part 5 again.

The polyaxial bone anchoring device can be used with rods of different diameters. In the case of using a rod with diameter D1 that is smaller than the diameter D, the deformable elements 66a, 66b may not be completely deformed outward, and thus the increase of pressure on the head 3 may be lower than with a rod with the diameter D, as discussed above. In order to obtain a friction hold of the rod between the deformable elements 66a, 66b, the distance between opposite rod retention grooves 69 must be the same or smaller than the diameter of the rod.

A second embodiment of the polyaxial bone anchoring device will be explained with reference to FIGS. 19a to 19d. Parts and portions that are identical or similar to the parts and portions of the first embodiment are marked with the same reference numerals, and the descriptions thereof will not be repeated. The polyaxial bone anchoring device according to the second embodiment has a receiving part 5' that additionally has second transverse holes 57', 58' that are located beneath the transverse holes 57, 58 that are configured to hold the pin members 107, 108. More specifically, the second transverse holes 57', 58' extend completely through the legs 54, 55 of the receiving part 5', at approximately the middle of the legs 54, 55 in a circumferential direction. As depicted, for example in FIG. 19a, the pressure member 6' includes deformable elements 66a', 66b' that are in a pre-locking position markedly bent inwards toward the central axis C. The deformable elements 66a', 66b' do not have rod retention grooves like groove 69 on the deformable elements 66a, 66b of the pressure member 6 the first embodiment. In the pre-locking position, the deformable elements 66a', 66b' are supported by the upper wall of the first front recess 115 of the pin members 107, 108, and the narrowing portion 52b of the receiving part 5' and the narrowing portion 613 of the pressure member 6' are in engagement. In the first configuration of the deformable elements 66a', 66b', there is a smallest distance $d_1$ defined between the inner surfaces of the deformable elements 66a', 66b' that is smaller than the diameter D of the rod 100. As can be further seen in FIG. 19a, the second transverse holes 57', 58' are located at such an axial height that the holes 57', 58' allow access to the deformable elements 66a', 66b' to deform the deformable elements 66a', 66b', for example, back from a second configuration into the first configuration.

Figures 19A, 19B, 19C, 19D:
FIGS. 19a to 19d show cross-sectional views of steps of using a polyaxial bone anchoring device according to a second embodiment with a rod.
Figures 20, 21, 22, 23:
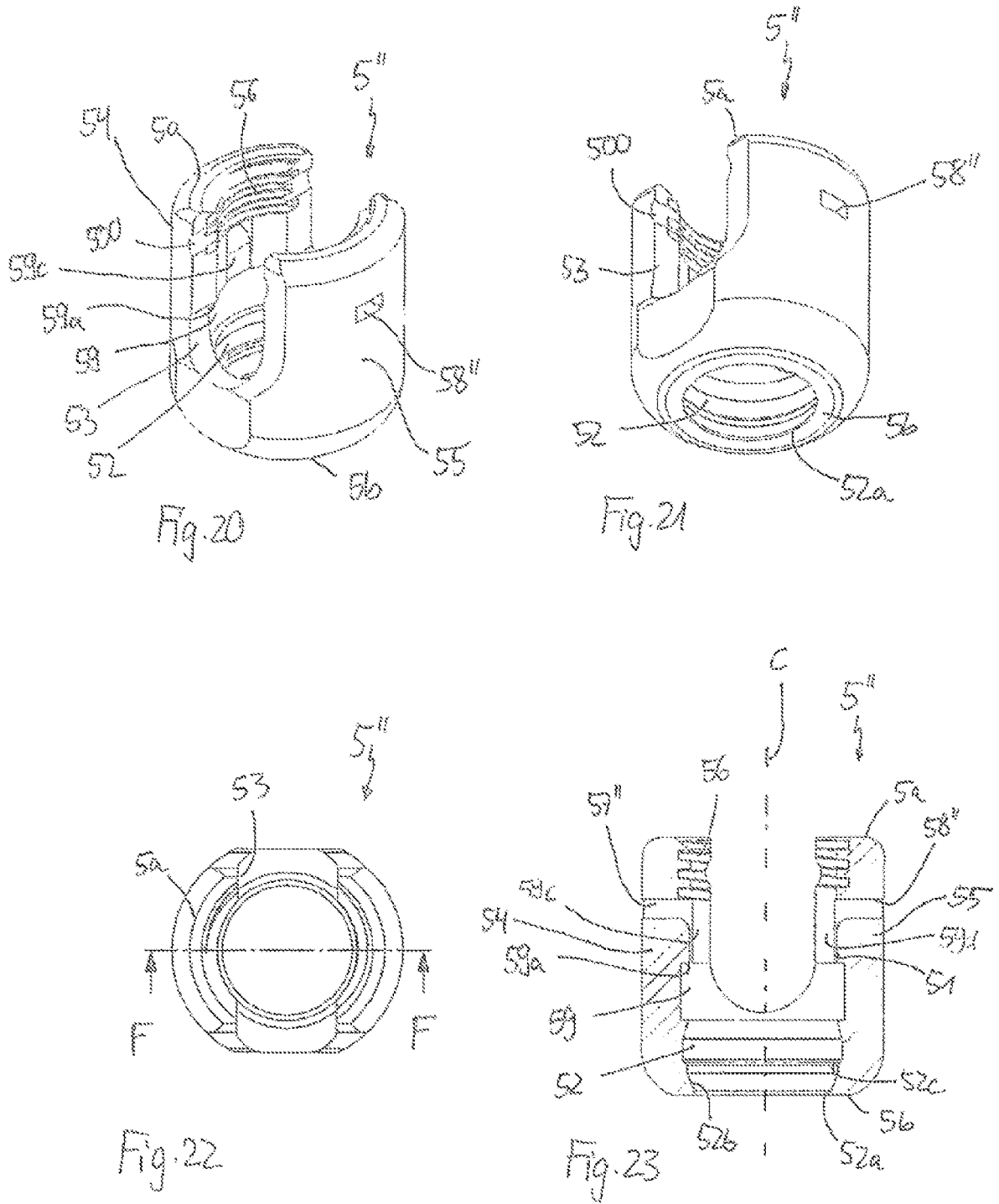
FIG. 20 shows a perspective view from a top of a receiving part of a polyaxial bone anchoring device according to a third embodiment.
FIG. 21 shows a perspective view from a bottom of the receiving part of FIG. 20.
FIG. 22 shows a top view of the receiving part of FIGS. 20 and 21.
FIG. 23 shows a cross-sectional view of the receiving part of FIGS. 20 to 22, the cross-section taken along line F-F in FIG. 22.

As illustrated in FIG. 19b, when the rod 100 is advanced further downward into the channel, the rod 100 passes between the portions of the deformable elements 66a', 66b' defining the smallest distance $d_1$. At a certain position, the deformable elements 66a', 66b' snap outward, thereby straightening and moving the bottom of the pressure member 6' further downward. By means of this, the pressure onto the head 3 is increased and the polyaxial movement of the head 3 relative to the receiving part 5' is restricted or locked, as shown in FIG. 19c. When the deformable elements 66a', 66b' are bent outward as depicted in FIG. 19c, the rod 100 may have no or only a little contact with the deformable elements 66a', 66b'. Hence, the rod 100 is freely movable in this position, while the position of the head 3 is locked or almost locked relative to the receiving part 5'.

If the rod 100 is moved upward, as illustrated in FIG. 19d, the deformable elements 66a', 66b' remain in their outwardly bent second configuration, and therefore, the locking of the head 3 is also maintained. In this embodiment, when it is necessary to release the pressure on the head 3 or to unlock the head 3, an instrument can be applied through the second transverse holes 57', 58' to push the deformable elements 66a', 66b' from the second configuration back to the first configuration.

As in the first embodiment, when the rod 100 is fully inserted relative to the pressure member 6, the locking element 7 can be inserted and tightened to finally lock the rod 100 and the head 3 relative to the receiving part 5'.

A third embodiment of the polyaxial bone anchoring device will now be described, with reference to FIGS. 20 to 31d. Parts and portions that are identical or similar to those of the first and second embodiments are marked with the same reference numerals, and the descriptions thereof will not be repeated. The receiving part 5" of the polyaxial bone anchoring device according to the third embodiment, as depicted in FIGS. 20 to 23, does not have the circular transverse holes 57, 58 of the receiving part 5 in the first embodiment. The receiving part 5" instead has rectangular transverse holes 57", 58" that are provided at approximately the middle of each leg 54, 55 in a circumferential direction, and at an axial position such that they are located slightly beneath or below a lower end of the internal thread 56. The holes 57", 58" have a rectangular cross-section which is oriented such that a long side of the rectangle is arranged in the circumferential direction and a short side of the rectangle is arranged in the axial direction. The size of the holes 57", 58" is such that the holes 57", 58" are configured to accommodate the free ends 67, and a portion adjacent to the free ends 67, of the deformable elements 66a", 66b" in a press-fit manner, for example, as shown in FIGS. 31a to 31d.

In addition, the receiving part 5" has a coaxial second bore 59 between the accommodation space 52 and the first coaxial bore 51. An inner diameter of the coaxial second bore 59 is greater than an inner diameter of the coaxial first bore 51, so that a shoulder 59a is formed between the coaxial second bore 59 and the coaxial first bore 51. The shoulder 59a serves as a stop for the pressure member 6", to limit the movement of the pressure member 6" in the upward direction. Moreover, two axial recesses 59c, 59d that extend into an inner wall of the receiving part 5" from the transverse holes 57", 58" to the coaxial second bore 59 are provided. A width of the axial recesses 59c, 59d in a circumferential direction corresponds to a width of the transverse holes 57", 58".

The pressure member 6" of the third embodiment differs from the pressure members 6, 6' of the previous embodiments by the design of the first portion 61". The second portion 610 is identical or similar to the second portions 610 of the previous embodiments. The first portion 61" is substantially cylinder segment-shaped and includes two side flanges 620a, 620b that are provided on opposite sides of the first portion 61" and that also have cylindrical outer surface portions. At the top surface 6a of the pressure member 6" and between the flanges 620a, 620b, a rod supporting surface 62a" is formed as a substantially V-shape groove to support rods of different diameters. Furthermore, in the top surface 6a two recesses 640a, 640b are formed that extend from the flanges 620a, 620b into the coaxial bore 615. Hence, the recesses 640a, 640b are located on either side of the rod supporting surface 62a". A contour of the recesses 640a, 640b is substantially rectangular. A width or thickness of the recesses 640a, 640b in a radial direction is greater than a width of the deformable elements 66a", 66b" described below, such that the deformable elements 66a", 66b" can move in a radial direction in the recesses 640a, 640b. A width of the recesses 640a, 640b in a direction along the rod supporting surface 62a" is at least as large as the width of the deformable elements 66a", 66b" in the same direction.

Figures 24, 25, 26, 27, 28, 29, 30:
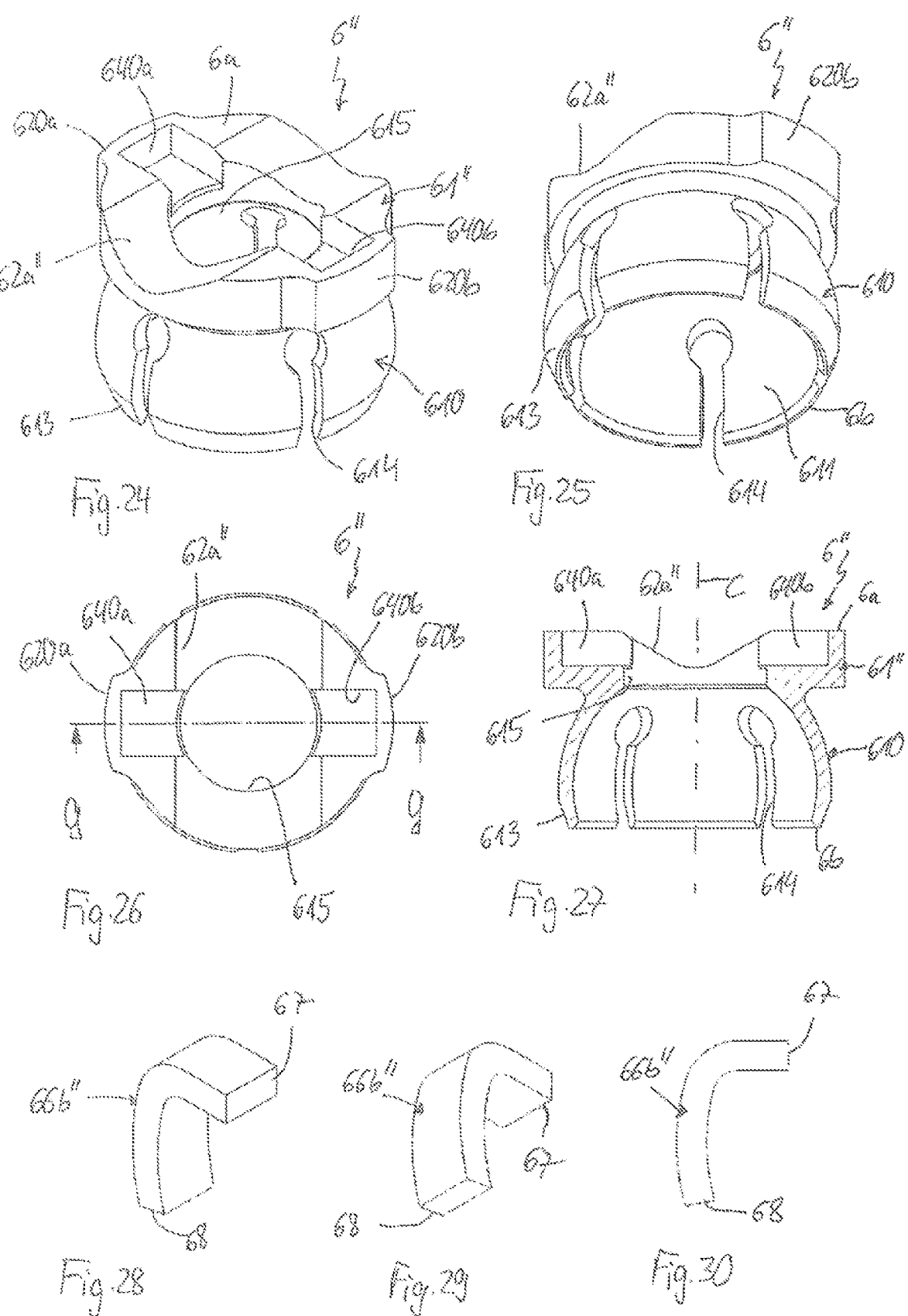
FIG. 24 shows a perspective view from a top of a pressure member of the polyaxial bone anchoring device according to the third embodiment.
FIG. 25 shows a perspective view from a bottom of the pressure member of FIG. 24.
FIG. 26 shows a top view of the pressure member of FIGS. 24 and 25.
FIG. 27 shows a cross-sectional view of the pressure member of FIGS. 24 to 26, the cross-section taken along line g-g in FIG. 26.
FIG. 28 shows a front perspective view of a deformable portion of the pressure member of the polyaxial bone anchoring device according to the third embodiment.
FIG. 29 shows a rear perspective view of the deformable portion shown in FIG. 28.
FIG. 30 shows a side view of the deformable portion shown in FIGS. 28 and 29.

Next, as depicted in FIGS. 28 to 30, the deformable elements 66a", 66b" have a substantially rectangular cross-section and an approximate inverted L-shape, with a long side and a short side. The short side is adjacent to the free end 67 that is to be inserted into the transverse holes 57", 58" of the receiving part 5", and the long side is adjacent to the lower end 68. The long side is slightly bent outward (i.e., away from a direction of extension of the short side). The deformable elements 66a", 66b" in this embodiment are separate parts that are not fixedly connected to a main portion of the pressure member 6", including the first portion 61 and the second portion 610. Referring to FIG. 31a, the bone anchoring device according to the third embodiment is pre-assembled as follows. The pressure member 6" is inserted from the top end 5a of the receiving part 5" in such a manner that the flanges 620a, 620b are oriented along the U-shaped recess 53 of the receiving part 5", until the first portion 61" of the pressure member 6" enters the coaxial second bore 59. Then, the pressure member 6" is rotated until the recesses 640a, 640b are on the side of or aligned with legs 54, 55 of the receiving part 5". The deformable elements 66a", 66b" are connected in a press-fit manner to the receiving part 5" so that their free upper ends 67 and their short portions are fixed in the transverse holes 57", 58" of the receiving part 5". The lower ends 68 are free relative to the receiving part 5". In the insertion position that is depicted in FIG. 31a, the upper surface 6a of the pressure member 6" abuts against the shoulder 59a of the coaxial second bore 59, and the free lower ends 68 of the deformable elements 66a", 66b" extend into the coaxial bore 615 of the pressure member 6". The deformable elements 66a", 66b" hold the pressure member 6" in the insertion position in a manner such that the deformable elements 66a", 66b" press elastically against the inner surface of the coaxial bore 615 of the pressure member 6".

FIG. 31b depicts the pre-locking position of the pressure member 6". This position is achieved by pulling the receiving part 5" upward relative to the pressure member 6" so that the narrowing portion 613 of the pressure member 6" cooperates with the narrowing portion 52b of the accommodation space 52 of the receiving part 5". When pulling the receiving part 5" upward, the lower ends 68 of the deformable elements 66a", 66b" snap into the recesses 640a, 640b, respectively, that are provided in the top surface 6a of the pressure member 6". Next, when the rod 100 is inserted as shown in FIG. 31b, the rod 100 presses or pushes the lower free ends 68 of the deformable elements 66a", 66b" radially outwards towards the outermost ends of the recesses 640a, 640b, respectively. Thereby, the deformable elements 66a", 66b" are bent outwards, so that the longer portions assume a substantially straight shape. As shown in FIG. 31c, when the rod 100 has been moved downward until it rests on the rod supporting surface 62a", the longer portion of the deformable elements 66a", 66b" is substantially straight. Thereby, the pressure member 6" has been moved downward so that the head 3 is locked. The rod 100 is also maintained in this position by the counterforce exerted onto the rod 100 by the deformable elements 66a", 66b". In this configuration, the rod 100 can be moved along its longitudinal rod axis by applying a force onto the rod 100 that is greater than the friction force exerted by the deformable elements 66a", 66b".

When or if the rod 100 is moved upward, for example, as depicted in FIG. 31d, the deformable elements 66a", 66b" can deform back to their original bent configuration so that they no longer exert a downward force onto the pressure member 6", and the head 3 can be unlocked.

It shall be understood that the dimensions and the sizes of the parts in the above described embodiments can be adjusted or varied in such a manner that the rod can cause a full locking of the head via the deformable elements of the pressure member, or can instead achieve only a friction hold of the head with a desired friction force. After a correct or desired position of the head and the rod has been found or reached, the polyaxial anchoring device can then be fully locked by the locking member.

Further modifications of the above described embodiments are also conceivable. For example, the deformable elements may have different shapes, as long as a deformation from a first configuration to a second configuration is possible. Even one single deformable element may be sufficient in some embodiments. In some embodiments, the pressure member can be a monolithic piece with the deformable elements integrated, for example, a piece made of or including a material exhibiting high elasticity, such as a super-elastic NiTi alloy, for example, Nitinol. Also, the V-groove for supporting rods having different diameters can be omitted, and a flat or curved rod supporting surface may be provided instead.

In addition, while a bottom loading polyaxial bone anchoring device has been described in the embodiments above, it shall be understood that the invention also encompasses top loading polyaxial bone anchoring devices, where the bone anchoring element is inserted from the top end of the receiving part. Various shapes of pressure members that are suitable for top loading polyaxial bone anchoring devices can be used. For example, the lower portion of the pressure member does not need to be flexible in such embodiments.

Meanwhile, for the locking member, various kinds of locking members are conceivable, such as two-piece or multi-piece locking members, outer nuts, etc.

For the bone anchoring element, different kinds of bone anchoring elements can also be used, such as screws, nails, cannulated anchors, hooks, etc. In some embodiments, the head and the shank may be constructed from two pieces that connect together. Although the head in the described embodiments is shown to have a spherical segment shape, in a manner such that the bone anchoring element is polyaxially pivotable with respect to the receiving part, in some embodiments, the head and/or the receiving part or the pressure member may instead be designed such that pivoting can only take place, for example, in one single plane. The polyaxial bone anchoring device may also be designed such that enlarged pivot angles in one or more particular directions are possible.

For the rod, all kinds of rods can also be used, such as rods with a smooth or a roughened surface, threaded rods, etc. The rod may be made from or include a solid material, may be cannulated, may have flexible portions, or may itself be made from a flexible material.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A polyaxial bone anchoring device comprising:
a receiving part having a first end, a second end below the first end, a longitudinal axis extending through the first end and the second end, a channel at the first end for receiving a rod, an engagement surface at the first end for engaging a locking member to lock the rod in the receiving part, and an accommodation space at the second end for pivotably holding the head;
a pressure member positionable in the receiving part and comprising a pressure exerting surface configured to exert pressure on a head of a bone anchoring element to lock the head relative to the receiving part; and
an expandable member having a first end directly engageable with the receiving part and an opposite second end directly engageable with the pressure member, wherein the expandable member is axially expandable in a direction of the longitudinal axis from a first configuration to a second configuration while a radial position of at least the first end of the expandable member relative to the longitudinal axis remains constant to urge the pressure member towards the second end of the receiving part to exert pressure on an inserted head; and
wherein the entire expandable member is positioned lower axially than the entire engagement surface of the receiving part, and wherein the pressure member is prevented from extending to an axial position that is higher than the first end of the expandable member.

2. The polyaxial bone anchoring device of claim 1, wherein the expandable member comprises a deformable portion configured to deform at least partially in a direction transverse to the longitudinal axis.

3. The polyaxial bone anchoring device of claim 1, wherein the second end of the expandable member is fixedly connected to the pressure member.

4. The polyaxial bone anchoring device of claim 1, wherein the expandable member is directly accessible from the channel for the rod.

5. The polyaxial bone anchoring device of claim 4, wherein the expandable member extends at least partially into the channel for the rod.

6. The polyaxial bone anchoring device of claim 1, wherein the expandable member is adjustable from the second configuration back to the first configuration.

7. The polyaxial bone anchoring device of claim 1, wherein when the expandable member is adjusted to the second configuration, the expandable member is configured to remain at the second configuration absent any forces from outside the bone anchoring device.

8. The polyaxial bone anchoring device of claim 1, wherein the expandable member and the pressure member are separate parts and separable from one another.

9. The polyaxial bone anchoring device of claim 1, wherein the expandable member comprises two expandable members respectively located on either side of the channel for the rod.

10. A polyaxial bone anchoring device comprising:
a bone anchoring element comprising a shank for anchoring to a bone and a head;
a receiving part having a first end, a second end, a longitudinal axis extending through the first end and the second end, a channel at the first end, and an accommodation space for pivotably holding the head, the accommodation space forming an opening at the second end for inserting the head;
a pressure member positionable in the receiving part and comprising a pressure exerting surface configured to exert pressure on the head to lock the head relative to the receiving part;
a rod insertable into the channel; and
an expandable member comprising an engagement surface configured to engage the rod;
wherein when the pressure member and the expandable member are in the receiving part at an insertion position, the head is insertable through the opening at the second end into and configured to be held in the receiving part, and thereafter the pressure member and the expandable member are adjustable from the insertion position to a pre-locking position to restrict removal of the head through the opening; and
wherein when the head, the pressure member, and the expandable member are in the receiving part at the pre-locking position, the rod is insertable into the channel and configured to directly engage the engagement surface of the expandable member to axially expand the expandable member in a direction of the longitudinal axis from a first configuration to a second configuration to urge the pressure member towards the second end of the receiving part to exert pressure on the head, and is configured to block adjustment of the expandable member back to the first configuration.

11. The polyaxial bone anchoring device of claim 10, wherein the expandable member comprises a deformable portion configured to deform at least partially in a direction transverse to the longitudinal axis.

12. The polyaxial bone anchoring device of claim 11, wherein the rod is configured to block the deformable portion from deforming in the direction transverse to the longitudinal axis.

13. The polyaxial bone anchoring device of claim 10, wherein the expandable member is fixedly connected to the pressure member.

14. The polyaxial bone anchoring device of claim 10, wherein the expandable member and the pressure member are separate parts and separable from one another.

15. The polyaxial bone anchoring device of claim 10, wherein the expandable member is adjustable from the second configuration back to the first configuration when the rod is spaced apart from the channel.

16. The polyaxial bone anchoring device of claim 10, wherein when the expandable member is at the second configuration, the pressure member exerts a force on the head to hold an angular position of the head relative to the receiving part.

17. The polyaxial bone anchoring device of claim 10, further comprising a compressible portion configured to hold the head in the receiving part and to exert a pressure directed towards the first end of the receiving part on the head.

18. The polyaxial bone anchoring device of claim 17, wherein the compressible portion is formed as part of the pressure member.

19. A polyaxial bone anchoring device comprising:
a receiving part having a first end, a second end, a longitudinal axis extending through the first end and the second end, a channel at the first end for receiving a rod, and an accommodation space at the second end for pivotably holding the head;
a pressure member positionable in the receiving part and comprising a pressure exerting surface configured to exert pressure on a head of a bone anchoring element to lock the head relative to the receiving part; and an expandable member having a first end fixedly connected to the receiving part in an unadjustable manner and an opposite second end configured to engage the pressure member, wherein the expandable member is axially expandable in a direction of the longitudinal axis from a first configuration to a second configuration to urge the pressure member towards the second end of the receiving part to exert pressure on an inserted head.

20. The polyaxial bone anchoring device of claim 19, wherein the expandable member is directly engageable with the pressure member.

* * * * *